(12) United States Patent
Cabot

(10) Patent No.: US 12,185,956 B2
(45) Date of Patent: Jan. 7, 2025

(54) ARRANGEMENTS AND METHODS IN THE PREPARATION OF THE PROXIMAL SURFACE OF THE TIBIA AND/OR FEMUR AND POSTERIOR FEMORAL CONDYLE PROXIMAL SURFACES FOR THE COMPONENTS OF A PROSTHETIC KNEE JOINT

(71) Applicant: Jonathan Peter Cabot, North Adelaide (AU)

(72) Inventor: Jonathan Peter Cabot, North Adelaide (AU)

( * ) Notice: Subject to any disclaimer, the term of this patent is extended or adjusted under 35 U.S.C. 154(b) by 989 days.

(21) Appl. No.: 17/271,306

(22) PCT Filed: Aug. 30, 2019

(86) PCT No.: PCT/AU2019/050922
§ 371 (c)(1),
(2) Date: Feb. 25, 2021

(87) PCT Pub. No.: WO2020/041839
PCT Pub. Date: Mar. 5, 2020

(65) Prior Publication Data
US 2021/0236147 A1    Aug. 5, 2021

(30) Foreign Application Priority Data
Aug. 31, 2018   (AU) ................................ 2018903218

(51) Int. Cl.
*A61B 17/17* (2006.01)
*A61B 17/15* (2006.01)
(Continued)

(52) U.S. Cl.
CPC ........ *A61B 17/1764* (2013.01); *A61B 17/155* (2013.01); *A61B 17/157* (2013.01);
(Continued)

(58) Field of Classification Search
CPC .. A61F 2002/30168; A61F 2002/30538; A61F 2002/3863; A61F 2002/4632;
(Continued)

(56) References Cited

U.S. PATENT DOCUMENTS

| 2009/0209884 | A1 | 8/2009 | Van Vorhis et al. |
| 2010/0326187 | A1* | 12/2010 | Stein ................. A61B 5/6846 73/379.01 |

(Continued)

FOREIGN PATENT DOCUMENTS

| WO | 1996/025123 | 8/1996 |
| WO | 2011/011609 | 1/2011 |

*Primary Examiner* — Marcela I. Shirsat
(74) *Attorney, Agent, or Firm* — Renner, Kenner, Greive, Bobak, Taylor & Weber

(57) ABSTRACT

An arrangement for the preparation of the proximal surface of the tibia and/or the proximal surface of the distal end of the femur and the posterior femoral condyle for a tibia component and/or a femoral component of a prosthetic knee joint. The arrangement includes an electronic system arrangement that receives or measures data information to which the electronic system can utilise this information to communicate control of a blade and/or cutting implement to resect the proximal surface of the tibia and/or distal end of the femur and/or the posterior femoral condyle to required reference plane cuts that provide for balanced angular movement between the femoral component and the tibia component of the prosthetic knee joint throughout an arc of motion from extension, mid-flexion and flexion.

6 Claims, 17 Drawing Sheets

(51) Int. Cl.
    *A61B 34/10*     (2016.01)
    *A61B 34/20*     (2016.01)
    *A61B 34/30*     (2016.01)
    *A61F 2/38*     (2006.01)
    *A61F 2/46*     (2006.01)

(52) U.S. Cl.
    CPC .............. *A61B 34/20* (2016.02); *A61B 34/30* (2016.02); *A61F 2/3859* (2013.01); *A61F 2/389* (2013.01); *A61F 2/4684* (2013.01); *A61B 34/10* (2016.02); *A61B 2034/2048* (2016.02); *A61B 2034/2051* (2016.02); *A61B 2034/2059* (2016.02); *A61B 2562/0219* (2013.01); *A61B 2562/0223* (2013.01); *A61B 2562/0247* (2013.01); *A61F 2002/4632* (2013.01); *A61F 2/4657* (2013.01)

(58) Field of Classification Search
    CPC ...... A61F 2002/4658; A61F 2002/4666; A61F 2002/4668; A61F 2002/2892; A61F 2002/3895; A61F 2002/4205; A61F 2/3859; A61F 2/389; A61F 2/4684; A61B 2034/2051; A61B 2034/2059; A61B 34/10; A61B 34/20; A61B 34/30; A61B 17/155; A61B 17/157; A61B 17/1764; A61B 17/154; A61B 17/1675
    USPC .......................................................... 606/88
    See application file for complete search history.

(56) References Cited

U.S. PATENT DOCUMENTS

| | | | |
|---|---|---|---|
| 2015/0105782 A1* | 4/2015 | D'Lima | A61F 2/4657 606/90 |
| 2016/0081758 A1 | 3/2016 | Bonutti | |
| 2017/0333058 A1* | 11/2017 | Cabot | A61F 2/389 |
| 2018/0116739 A1 | 5/2018 | Gogarty | |
| 2018/0177612 A1 | 6/2018 | Trabish et al. | |
| 2019/0216608 A1* | 7/2019 | Cabot | A61F 2/4657 |

\* cited by examiner

ARRANGEMENTS AND METHODS IN THE PREPARATION OF THE PROXIMAL SURFACE OF THE TIBIA AND/OR FEMUR AND POSTERIOR FEMORAL CONDYLE PROXIMAL SURFACES FOR THE COMPONENTS OF A PROSTHETIC KNEE JOINT

FIELD OF THE INVENTION

This invention relates to improved arrangements and methods in the preparation of the proximal surface of the tibia and/or the distal end of the femur and posterior femoral condyle for the components of a prosthetic knee joint. More particularly, this invention relates to an improved way in which the final bone resections of these surfaces for the tibia and femur can be completed.

BACKGROUND ART DISCUSSION

The applicant as disclosed in WO2017181216 recognized the significance of establishing a 'tibia reference plane' that was defined by the orientation of the underside of the joint liner, wherein this tibia referenced plane when replicated as a final bone resection cut of the proximal surface of the tibia provided the necessary surface profile, such that when the tibia component of the prosthetic knee joint was implanted in the knee joint of the patient, it would be configured as to enable the required balance and stability between the tibia and femoral components of the prosthetic knee joint, whether that be a uni-compartmental knee replacement or a total knee replacement.

As further disclosed in WO2017181216 through the user operable height extension tabs that assisted in establishing the tibia reference plane by engagement of these user operable height extension tabs with the underside of the joint liner, a mounting arrangement was then utilized as a means to assist in the cutting process so as to replicate that tibia reference plane as the final bone resection to the proximal surface of the tibia.

The mounting arrangement in WO2017181216 utilised a mechanical structural arrangement that included a mounted engagement between the joint liner and a cutting guide arrangement.

The cutting guide included a slot such that in the first mounted position the slot would be aligned with the established tibia reference plane and then through a vertical support structure this indicator with the slot now aligned with the same orientation of the tibia reference plane could be lowered and as best summarised the cutting guide at the second mounted position would be located at the correct vertical position for cutting into new bone with the indicator slot of the cutting guide maintaining the correct orientation of the established tibia reference plane, so a blade or saw is then guided and orientated through the slot of the cutting guide to enable the final bone resection which then replicates the requisite profile of the tibia reference plane to the proximal surface of the tibia.

While it was possible to utilise these structural features of the mounting arrangement including the unique cutting guide with the slot that would be orientated in the alignment of the tibia reference plane to act as the guide for the blade or saw to complete the resection to replicate the established tibia reference plane to the bone of the tibia, it does involve the requirement to employ specific joint liners which are configured so that the mounting arrangement can be in part be mounted thereto.

It would be advantageous if there was a more convenient way to complete the cutting to replicate the established tibia reference plane which is to provide that profile of the proximal surface of the tibia for optimum stability and balance throughout the arc of motion in the artificial knee joint that one would expect from a normal healthy knee.

The applicant, by way of WO2017197462, was also able to previously provide methods and arrangements for the balancing of the femoral side of the prosthetic knee joint for optimum final bone resection of the distal end of the femur and also the posterior femoral condyle, and other femoral cuts to accommodate the femoral component.

As discussed in wo2017197462 the unique use of the generally L shaped femoral tibia stability gap alignment clamp provided a vertical arm with associated lateral extension tabs which were responsible for providing the requisite distal end of the femur reference plane through the engagement with the front plate, and the horizontal arm with the associated height extension tabs makes the necessary adjustments to the base plate (and/or separate sections of the base plate) to establish the requisite posterior condylar reference plane so that if the final resection of each of the distal end of the femur and the posterior femoral condyle where cut to expose surfaces with the same profile of these reference planes, this then allows the femoral component of the prosthetic knee joint to operate optimally.

Accordingly, while the applicant has previously been able to recognise unique ways and means to establish reference planes through the employment of the arrangements discussed in each of patents WO2017181216 and WO2017197462, it would be particularly advantageous to provide an improved way in which those reference planes of the tibia and femur can then be more efficiently and conveniently translated to the final bone resection profile cuts required for the proximal surface of the tibia and/or the distal end of the femur and posterior femoral condyle.

It is therefore an object of this invention to provide an improved arrangement and means to facilitate the final resection cuts for the proximal surface of the tibia and/or the distal end of the femur and posterior femoral condyle.

While referencing throughout the specification with respect to the femur relates in part to an improved arrangement and means to facilitate the final resection cuts to the distal end of the femur and posterior femoral condyle, this same improved arrangement and means can also facilitate other femoral cuts to accommodate the femoral component as required.

SUMMARY OF THE INVENTION

Accordingly in one form of the invention there is provided an arrangement for the preparation of the proximal surface of the tibia for a tibia component of a prosthetic knee joint, said arrangement including:
  a tibia and femoral stability gap preparation plate, said tibia and femoral stability gap preparation plate adapted to be placed upon the proximal surface of the tibia, said tibia and femoral stability gap preparation plate further including an upper side, said upper side having a plurality of user operable height adjustable extension tabs, wherein each user operable height adjustable extension tab is adapted to engage an underside of a joint liner, wherein said joint liner includes an upper articulated surface to engage a femoral component of a knee joint, such that a height adjustment of said plurality of user operable height adjustable extension tabs defines a measurement taken in each of extension, mid-flexion and flexion, wherein the measurement is commensurate with a tibia reference plane defined on an underside of the joint liner, wherein a final bone resection of the proximal surface of the tibia consistent with said tibia reference plane provides for balanced angular movement between the tibia component and the femoral component of a prosthetic knee joint throughout an arc of motion from extension, mid-flexion and flexion;

an electronic system arrangement including a measured or received input signal, wherein the measured or received input signal of the electronic system arrangement provides a tibia reference plane measured data information, wherein the tibia reference plane measured data information includes the orientation in space, angle and/or positioning of the tibia reference plane defined by the underside of the joint liner;

said electronic system arrangement configured to respond to the measured or received inputted signal of the tibia reference plane measured data information to communicate electrical energy in the form of an output action to align a blade and/or cutting implement at an angle such that resecting of tibia bone across at or below the proximal surface of the tibia at the alignment of the blade and/or cutting implement provided by the tibia reference plane measured data information replicates the tibia reference plane on the proximal surface of a final resected tibia proximal surface.

In a further form of the invention there is an arrangement for providing the proximal surface of the distal end of the femur and the posterior femoral condyle of the femur for a femoral component of a prosthetic knee joint, said arrangement including:

a generally L shaped femoral tibia stability gap alignment clamp mountable to the femur such that a vertical arm of the generally L shaped femoral tibia gap alignment clamp is adapted to be contiguous and/or aligned with the distal end of the femur and a horizontal arm of the generally L shaped femoral tibia gap alignment clamp is adapted to be contiguous and/or aligned with a posterior femoral condyle of the femur;

said vertical arm of the generally L shaped femoral tibia stability gap alignment clamp including user-operable lateral adjustable extension tabs, wherein each user-operable lateral adjustable extension tab is adapted to engage a front plate, such that lateral adjustment of the front plate by said plurality of user-operable lateral adjustable extension tabs provides a distal end of the femur reference plane defined by the front surface of the front plate, wherein a final bone resection of the distal end of the femur with a profile of the distal end of the femur reference plane provides balanced angular movement between the tibia component and the femoral component of the prosthetic knee joint throughout an arc of motion from extension, mid-flexion and flexion post surgery;

said horizontal arm of the generally L shaped femoral tibia stability gap alignment clamp includes user-operable height adjustable extension tabs adapted to adjust the vertical height of a base plate relative to the horizontal arm of the generally L shaped femoral tibia stability gap alignment clamp, such that vertical height adjustment of said plurality of user-operable height adjustable extension tabs upon the base plate defines a posterior femoral condyle reference plane wherein final bone resection with the posterior femoral condyle referenced plane to the posterior femoral condyle of the femur provides for balanced angular movement between the femoral component and the tibia component of the prosthetic knee joint throughout an arc of motion from extension, mid-flexion and flexion; and an electronic system arrangement including a measured or received input signal, wherein the measured or received input signal into the electronic system arrangement provides a distal end of the femur reference plane measured data information and/or a posterior femoral condyle reference plane measured data information;

said electronic system arrangement configured to respond to the measured or received inputted signal of the distal end of the femur reference plane measured data information and/or the posterior femoral condyle reference plane measured data information to communicate electrical energy in the form of an output action to align a blade and/or cutting implement at an angle and/or angles to resect the distal end of the femur and/or the posterior femoral condyle with a profile or profiles that replicate the distal end of the femur reference plane and/or the posterior femoral condyle reference plane.

In still a further form of the invention there is provided an arrangement for the preparation of the proximal surface of the tibia for a tibia component of a prosthetic knee joint, said arrangement including:

a joint liner, wherein said joint liner includes an upper articulated surface to engage a femoral component of a knee joint, said joint liner on an underside side including a plurality of user operable height adjustable extension tabs, wherein each user operable height adjustable extension tab is adapted to engage the proximal surface of the tibia and/or a plate, platform or other generally flat object on the surface of the tibia, such that a height adjustment of said plurality of user operable height adjustable extension tabs defines a measurement taken in each of extension, mid-flexion and flexion, wherein the measurement is commensurate with a tibia reference plane defined within and/or under the joint liner, wherein a final bone resection of the proximal surface of the tibia consistent with said tibia reference plane provides for balanced angular movement between the tibia component and the femoral component of a prosthetic knee joint throughout an arc of motion from extension, mid-flexion and flexion;

an electronic system arrangement including a measured or received input signal, wherein the measured or received input signal into the electronic system arrangement provides a tibia reference plane measured data information, wherein the tibia reference plane measured data information includes the orientation in space, angle and/or positioning of the tibia reference plane defined by the within and/or under the joint liner;

said electronic system arrangement configured to respond to the measured or received inputted signal of the tibia reference plane measured data information to communicate electrical energy in the form of an output action to align a blade and/or cutting implement at an angle such that resecting of the bone across at or below the proximal surface of the tibia at the alignment of the blade and/or cutting implement provided by the tibia reference plane measured data information replicates the tibia reference plane on the proximal surface of the final resected tibia.

In still an even further form of the invention there is provided an arrangement for providing the proximal surface of the distal end of the femur and the posterior femoral condyle of the femur for a femoral component of a prosthetic knee joint, said arrangement including:

a generally L shaped femoral tibia stability gap alignment device adapted to be positioned to the femur such that a vertical arm of the generally L shaped femoral tibia gap alignment clamp is adapted to be aligned with the distal end of the femur and a horizontal arm of the generally L shaped femoral tibia gap alignment device is adapted to be aligned with a posterior femoral condyle of the femur;

said vertical arm of the generally L shaped femoral tibia stability gap alignment device including user-operable lateral adjustable extension tabs, wherein each user-operable lateral adjustable extension tab is adapted to engage a distal end of the femur or a device mounted to the distal end of the femur, such that lateral adjustment by said plurality of user-operable lateral adjustable extension tabs provides a distal end of the femur reference plane defined by a front surface of the L shaped femoral tibia stability gap alignment device, wherein a final bone resection of the distal end of the femur with a profile of the distal end of the femur reference plane provides balanced angular movement between the tibia component and the femoral component of the prosthetic knee joint throughout an arc of motion from extension, mid-flexion and flexion post surgery;

said horizontal arm of the generally L shaped femoral tibia stability gap alignment device includes a plurality of user-operable height adjustable extension tabs such that vertical height adjustment of the plurality of user-operable height adjustable extension tabs upon the posterior femoral condyle or a device positioned on the posterior femoral condyle provides for a posterior femoral condyle reference plane on defined on the underside of the horizontal arm, wherein final bone resection with the posterior femoral condyle referenced plane to the posterior femoral condyle of the femur provides for balanced angular movement between the femoral component and the tibia component of the prosthetic knee joint throughout an arc of motion from extension, mid-flexion and flexion; and an electronic system arrangement including a measured or received input signal, wherein the measured or received input signal into the electronic system arrangement provides a distal end of the femur reference plane measured data information and/or a posterior femoral condyle reference plane measured data information;

said electronic system arrangement configured to respond to the measured or received inputted signal of the distal end of the femur reference plane measured data information and/or the posterior femoral condyle reference plane measured data information to communicate electrical energy in the form of an output action to align a blade and/or cutting implement at an angle and/or angles to resect the distal end of the femur and/or the posterior femoral condyle with a profile or profiles that replicate the distal end of the femur reference plane and/or the posterior femoral condyle reference plane.

In preference the electronic system arrangement includes a sensor arrangement wherein the sensor arrangement includes an accelerometer, gyroscope, a position sensor, an inductor sensor, a capacitive displacement sensor, laser sensor, optical sensor, pressure sensor, magnetic and magneto-inductor sensors, confocal sensors and/or draw-wire sensors and/or computer navigation to assist in providing the reference plane measured data.

In preference the sensor arrangement includes pressure sensor arrangement incorporated into the joint liner, tibia and femoral stability gap preparation plate or the generally L shaped femoral tibia stability gap alignment clamp.

In preference the arrangement further includes a robotic arm to which the blade and/or cutting implement is attached thereto said robotic arm.

In preference the robotic arm is under the control of the electronic system arrangement.

In preference the electronic system arrangement in one embodiment is configured to control the movement of the robotic arm to be placed in position to where the final bone resection is to be completed by way of the blade and/or cutting implement to which the electronic system arrangement has orientated said blade and/or cutting implement at the angle to complete the cut to the pre-determined reference plane profile.

In preference the electronic system arrangement includes a micro-controller.

In preference the electronic system arrangement includes and/or communicates with a display screen, to display measured information and/or action being carried out under control of said electronic system arrangement.

In preference the electronic system arrangement is configured and functional to control the user operable height adjustable extension tabs of the joint liner or tibia and femoral stability gap preparation plate for height adjustment of said plurality of user operable height adjustable extension tabs for measurement at each of extension, mid-flexion and flexion, wherein said measurement at each of extension, mid-flexion and flexion by the electronic system arrangement is commensurate with the tibia reference plane.

In preference the electronic system arrangement is configured and functional to control the user-operable lateral adjustable extension tabs and the user-operable height adjustable extension tabs of the generally L shaped femoral tibia stability gap alignment clamp for adjustment of said user-operable lateral adjustable extension tabs and the user-operable height adjustable extension tabs for measurement commensurate with the femur reference plane and the femoral condyle reference plane.

Advantageously, this invention has provided for an improved way in which the reference planes that were established by the arrangements for preparing the proximal surface of the tibia, the proximal surface of the distal end of the femur and the posterior femoral condyle of the femur can be utilised.

The electronic system arrangement is configured with the ability to be able to identify, measure and/or record the relevant reference planes and then with further inherent functionality of the electronic system arrangement is able to communicate this identified, measured and/or recorded reference planes to control the blade and/or cutting implement that is responsible for the final resection cuts of the bone.

In further preferred embodiments of the invention the electronic system arrangement would be adapted to control structural features like robotic arms to efficiently and conveniently bring the blade and/or cutting implement already orientated to the correct angle to reproduce the relevant reference planes, either with or without the guidance of a surgeon, to the knee joint, to complete the cut across the bone that is to be finally resected.

BRIEF DESCRIPTION OF THE DRAWINGS

FIGS. 4a and 4b show perspective views of the tibia and femoral stability gap preparation plate in a preferred embodiment of the invention wherein FIG. 4a shows the user operable extension tabs in a lowered position wherein FIG. 4b shows the user operable extension tabs in adjusted raised positions.

Figure 1:
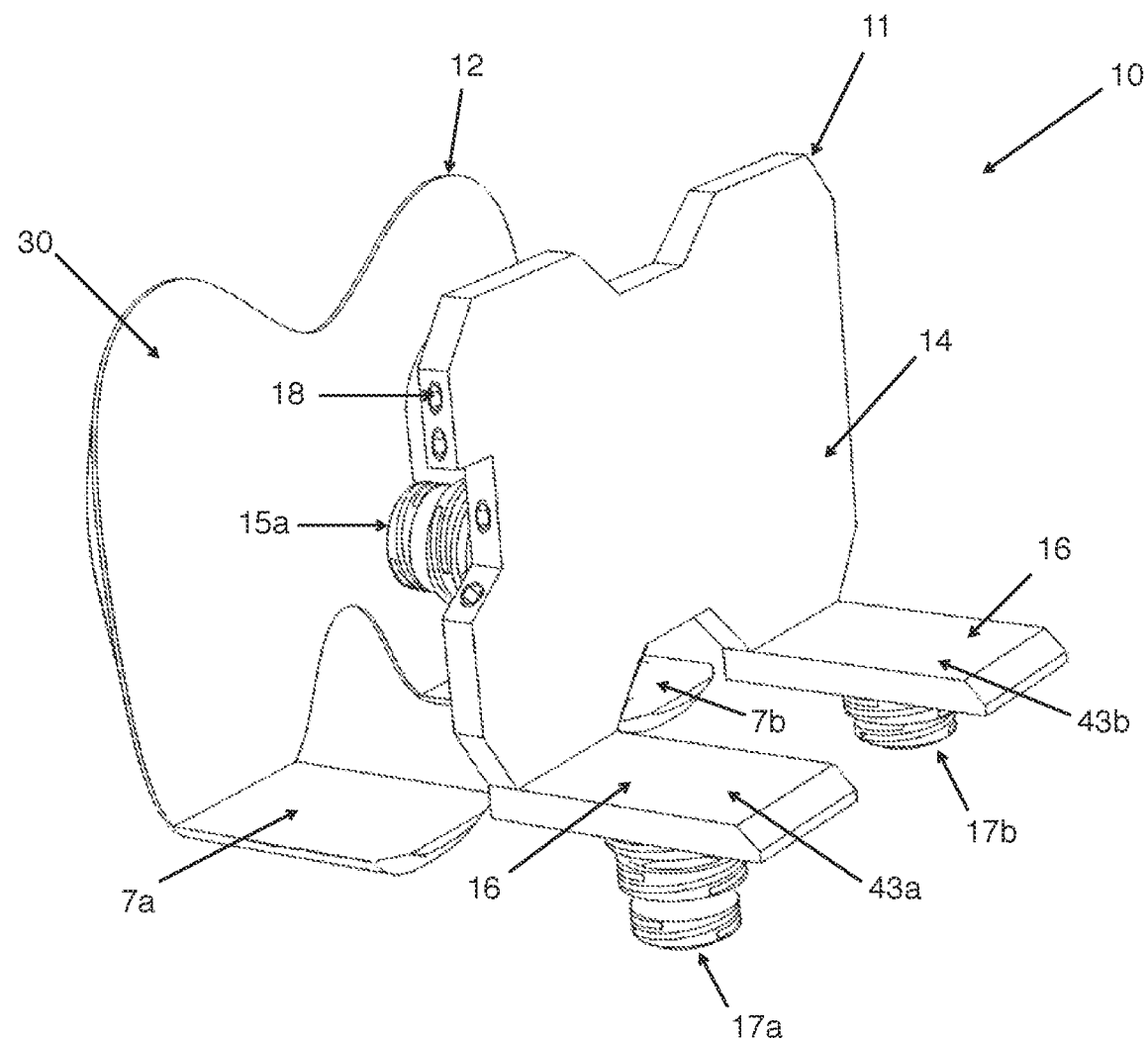
FIG. 1 is a rear perspective view of the generally L shaped femoral tibia stability gap alignment clamp and the front plate arrangement in a preferred embodiment of the invention.

The illustrations need to be placed in the context of the intended outcome achieved through the use of arrangement and methods provided for in this invention.

DETAILED DESCRIPTION OF THE DRAWINGS

Orthopaedic surgeons during surgery aim to provide balance, unobstructed movement of the knee components for the complete arc of motion from extension, mid-flexion and flexion and then back again.

Accordingly, the final bone resection of the proximal surface of the tibia and that of the distal end of the femur and the posterior femoral condyle is required to be cut correctly in order to present the appropriate profile to the tibia and femur prosthetic components positioning in the knee arthroplasty whether that be a total knee or uni-compartmental knee operation.

The establishment of the reference planes to be describe below help to achieve this outcome.

FIGS. 1 to 3h show the arrangement (10) that is responsible for the preparation of the distal end of the femur reference plane 70 shown as the broken lines in FIG. 3e, and the preparation of the posterior condyle reference plane 74 shown as broken lines in FIG. 3f of which information which will be discussed in greater detail below is inputted into the Electronic System Arrangement shown as 72, purely for a pictorial reference only, wherein this Electronic System Arrangement 72 is responsible in the preferred embodiment to control the robotic arm 78 and cutting blade 79 responsible for the final bone resections of the distal end of the femur 39 and the posterior femoral condyle 80.

The arrangement (10) includes the generally L shaped femoral tibia stability gap alignment clamp (11).

In the preferred embodiment the front plate (12) is a separate piece to the generally L shaped femoral tibia stability gap alignment clamp (11). The exterior surface of the front plate (12) is referenced as (28).

Figure 3A:
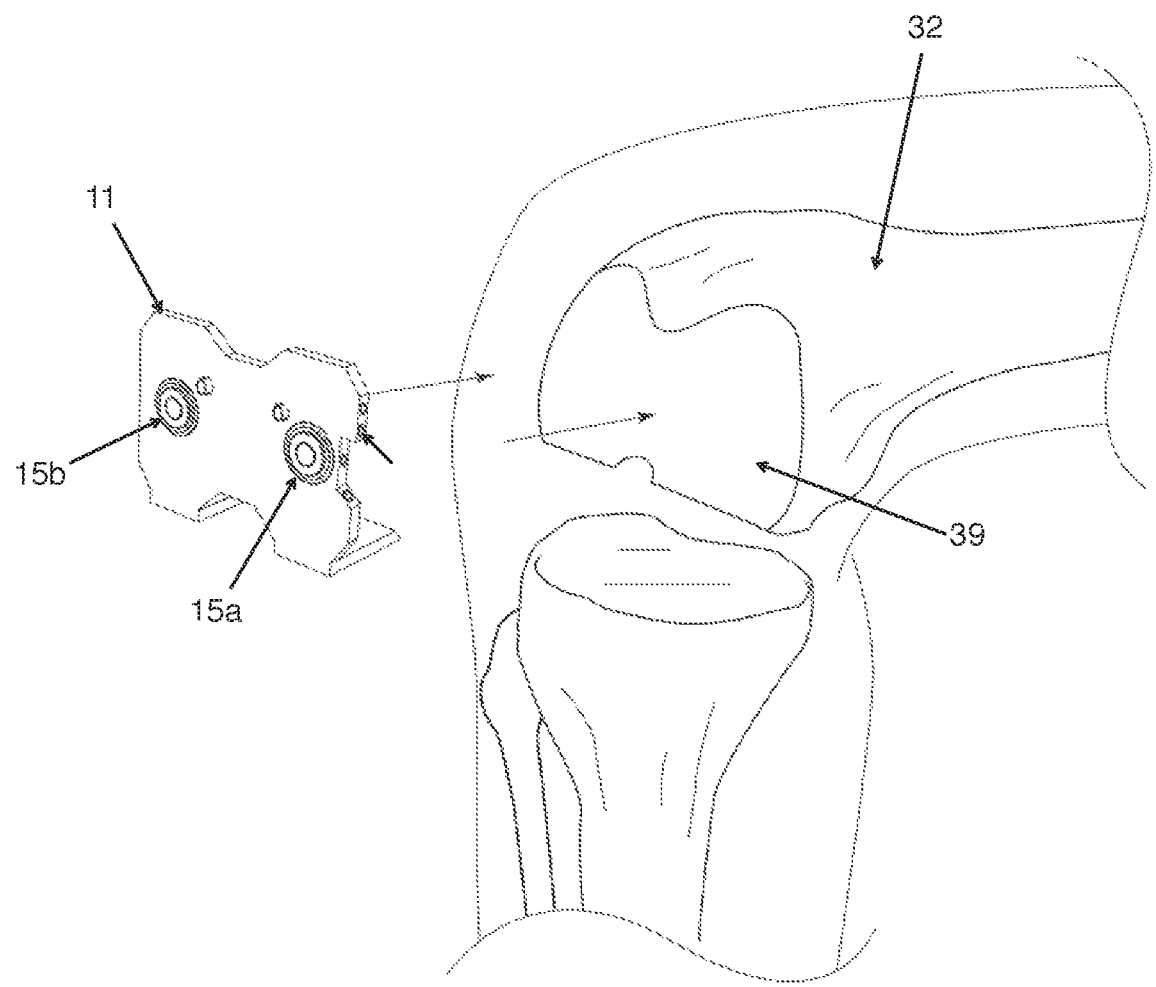
FIGS. 3a to 3h are schematic representations of a method by which the arrangement can be utilized in order to prepare and cut the final bone resections to the distal end of the femur and the posterior femoral condyle in a preferred embodiment of the invention.
Figure 3B:
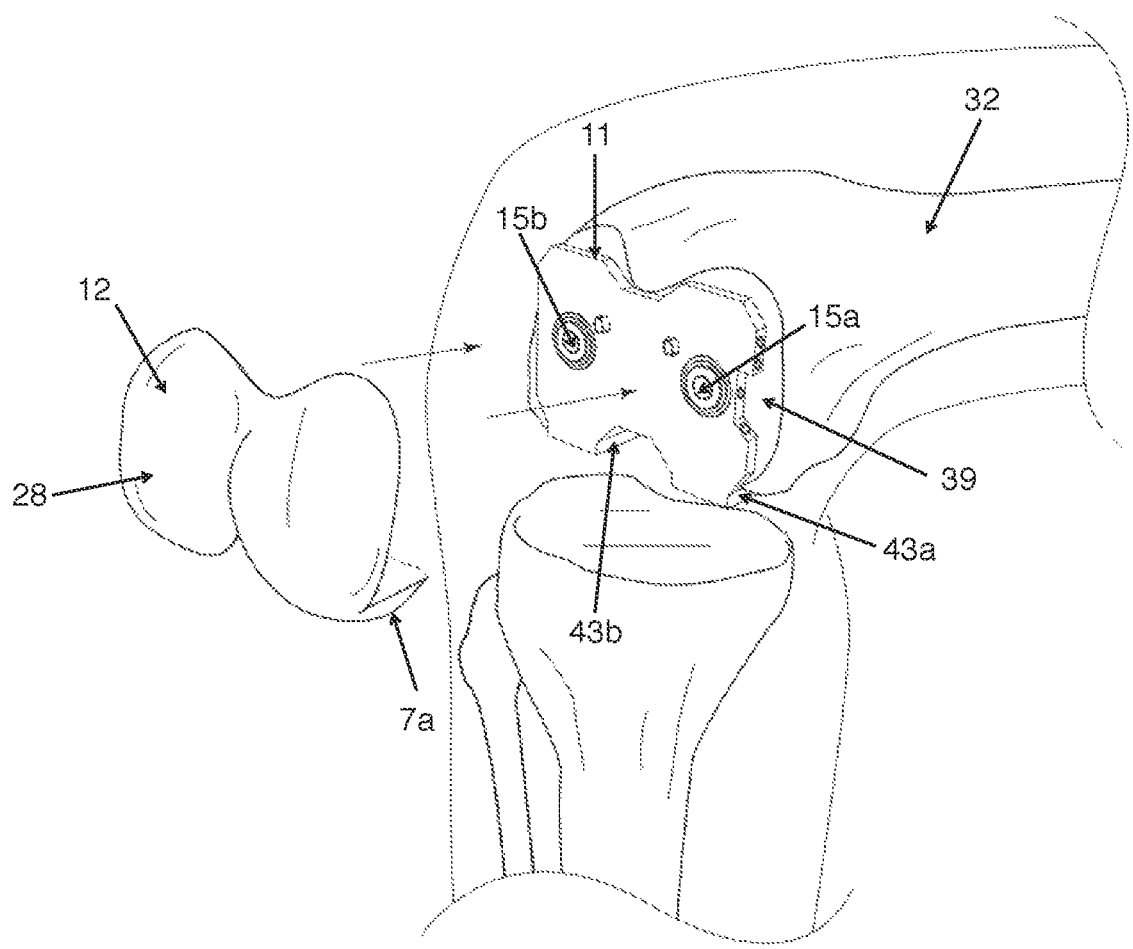
Figure 3C:
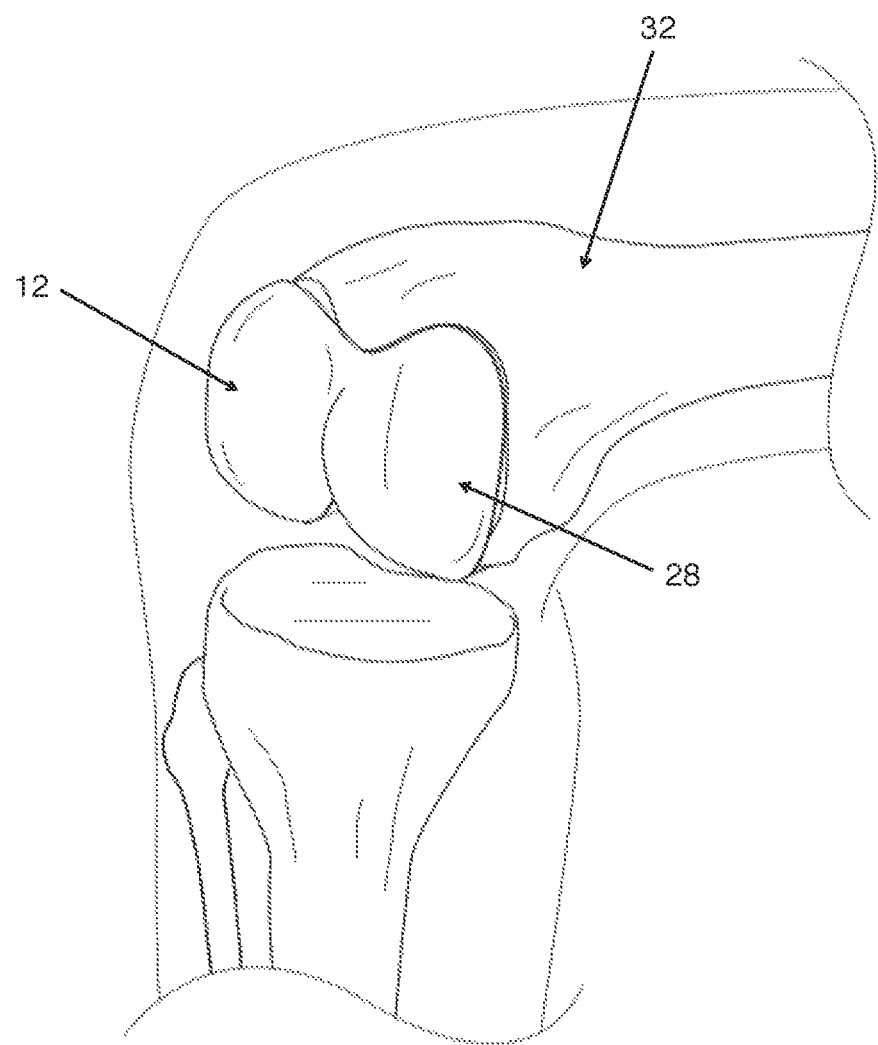
Figure 3D:
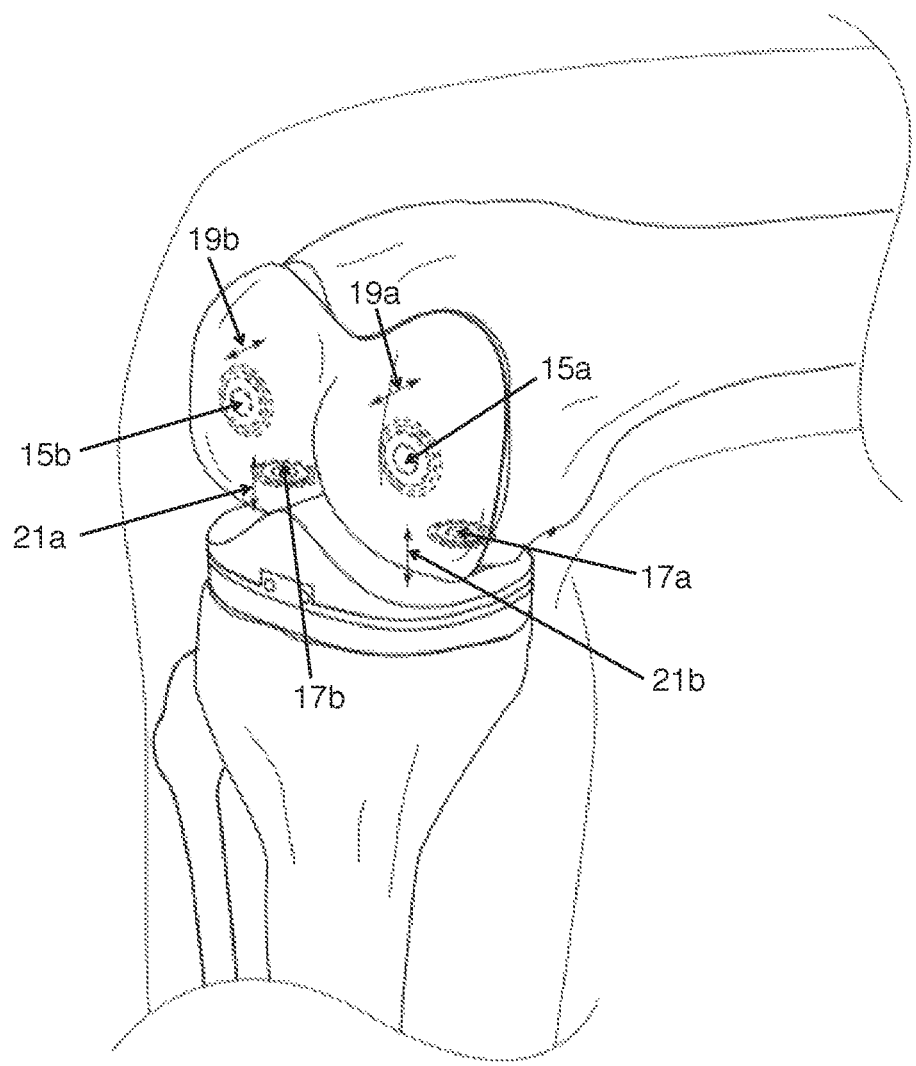

The front plate (12) is commensurate in dimensions with dimensions and shape of the distal end of the femur as best seen in FIG. 3a.

The base of the front plate (12) in the preferred embodiment includes separate sections (7a) and (7b), wherein each section (7a) and (7b) of the base of the front plate (12) is engaging below a corresponding user-operable height adjustable tab (17a) and (17b) on the respective sections (43a) and (43b) of the horizontal arm (16) of the generally L shaped femoral tibia stability gap alignment clamp (11).

In other embodiments not shown the front plate (12) and the base plate (7a) and (7b) can be integral as a single assembly with the generally L shaped femoral tibia stability gap alignment clamp (11).

Figure 2:
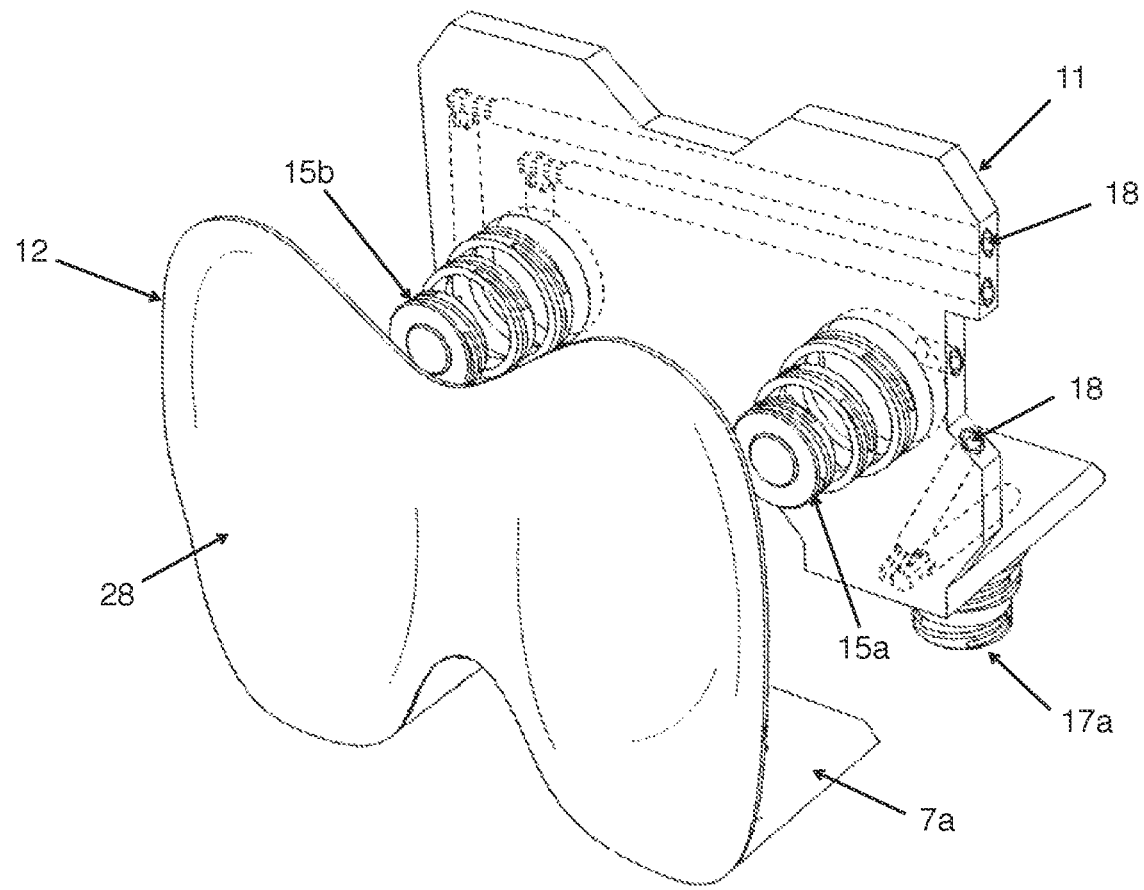
FIG. 2 is a front perspective view of the generally L shaped femoral tibia stability gap alignment clamp and the front plate arrangement in a preferred embodiment of the invention.

As best seen in FIGS. 1 and 2 the front plate (12) and the base plate sections (7a) and (7b) are all a single piece wherein the single piece forms a generally L shaped configuration replicating shape of femoral component commensurate with the configuration of the generally L shaped femoral tibia stability gap alignment clamp (11).

The horizontal arm (16) of the generally L shaped femoral tibia stability gap alignment clamp (11) as introduced above is in fact two sections (43a) and (43b) so that the horizontal arm (16) is configured generally consistent with the posterior femoral condyle (80) at the distal end of the femur 32.

The vertical arm (14) of the generally L shaped femoral tibia stability gap alignment clamp (11) includes the user-operable lateral adjustable tabs (15a) and (15b) which are adapted to engage the internal side (30) of the front plate (12) when the front plate (12) is mounted or connected to the generally L shaped femoral tibia stability gap alignment clamp (11).

In the preferred embodiment shown in FIGS. 1 and 2 there are two of the user-operable height adjustment tabs (17a) and (17b) and two user-operable laterally adjustable tabs (15a) and (15b).

Nonetheless there is no limit to the amount and/or orientation of the user-operable height and lateral adjustable extension tabs for this invention.

As will be discussed in greater detail shortly hereafter, the scope of the invention simply provides for incorporating a plurality of user-operable lateral extension tabs on the vertical arm (14) and a plurality of height adjustable extension tabs on the underside of the horizontal arm (16) of the generally L shaped femoral tibia stability gap alignment clamp (11).

Figure 3E:
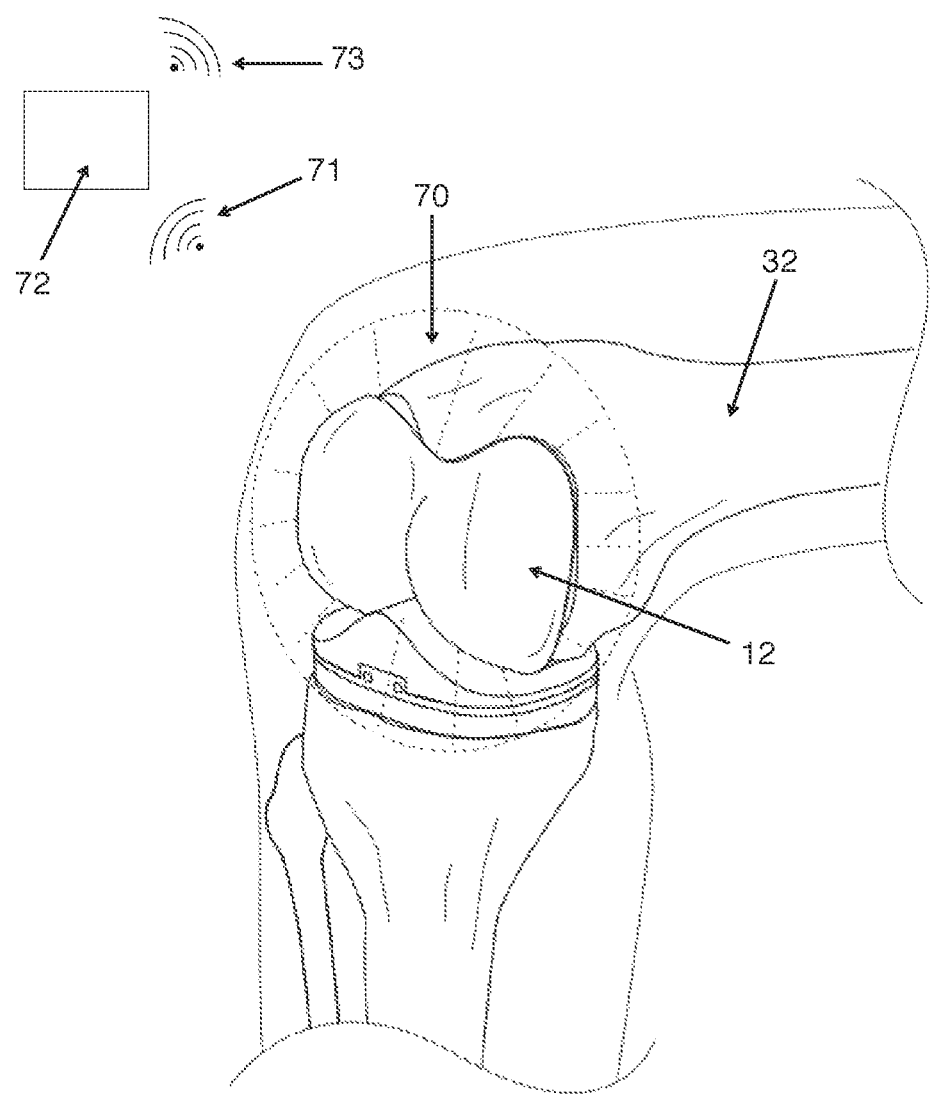
Figure 3F:
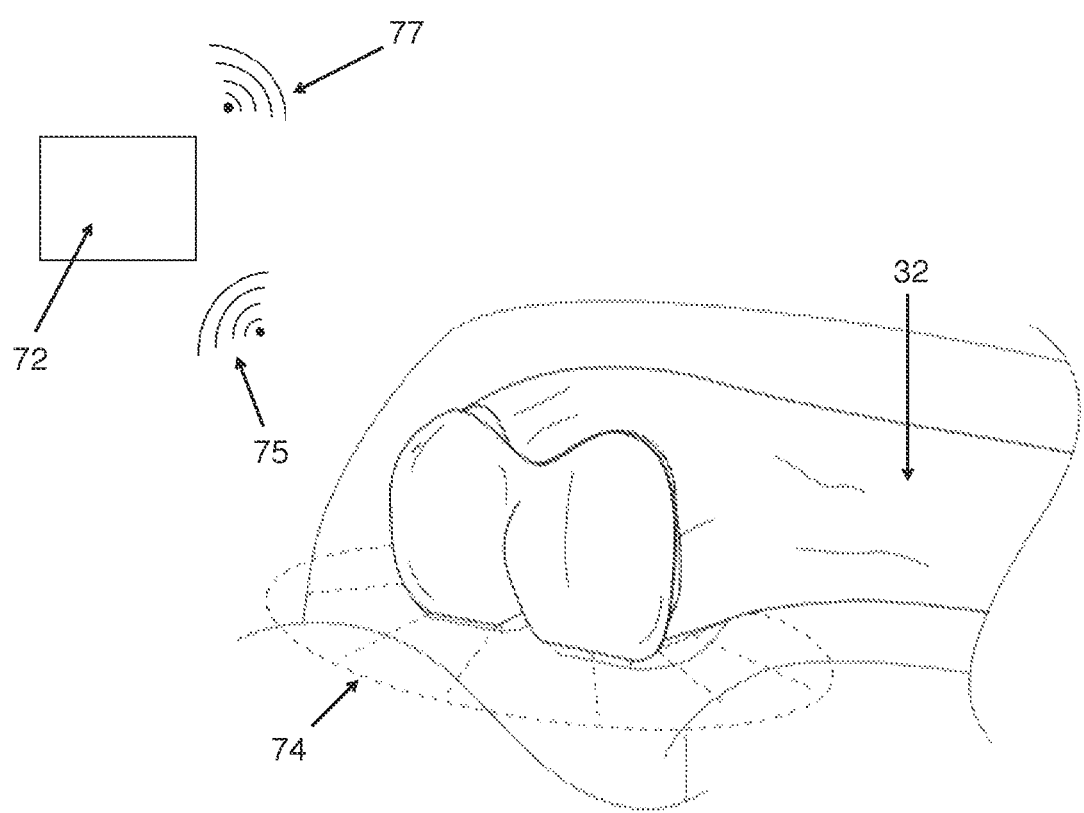
Figure 3G:
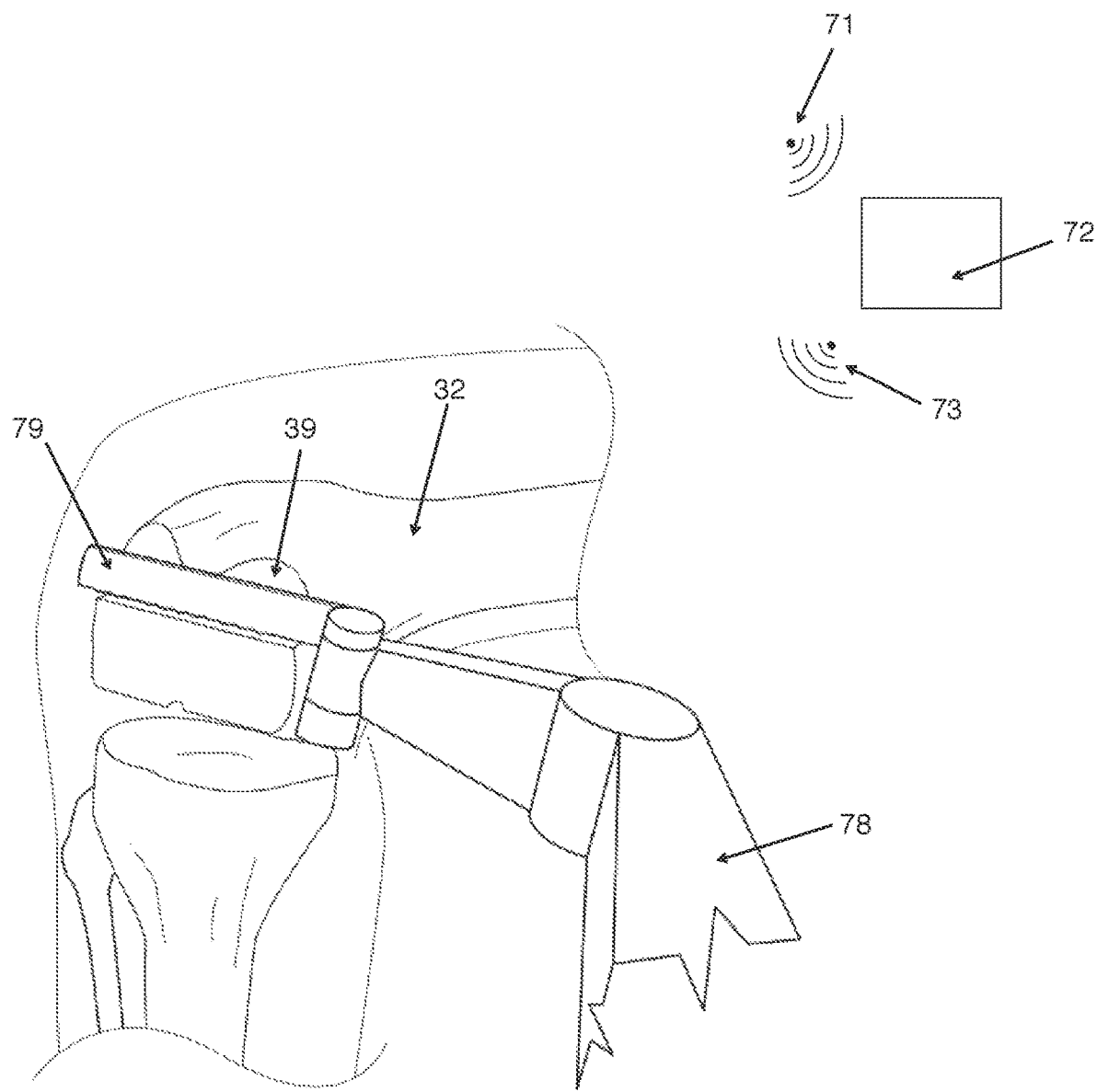
Figure 3H:
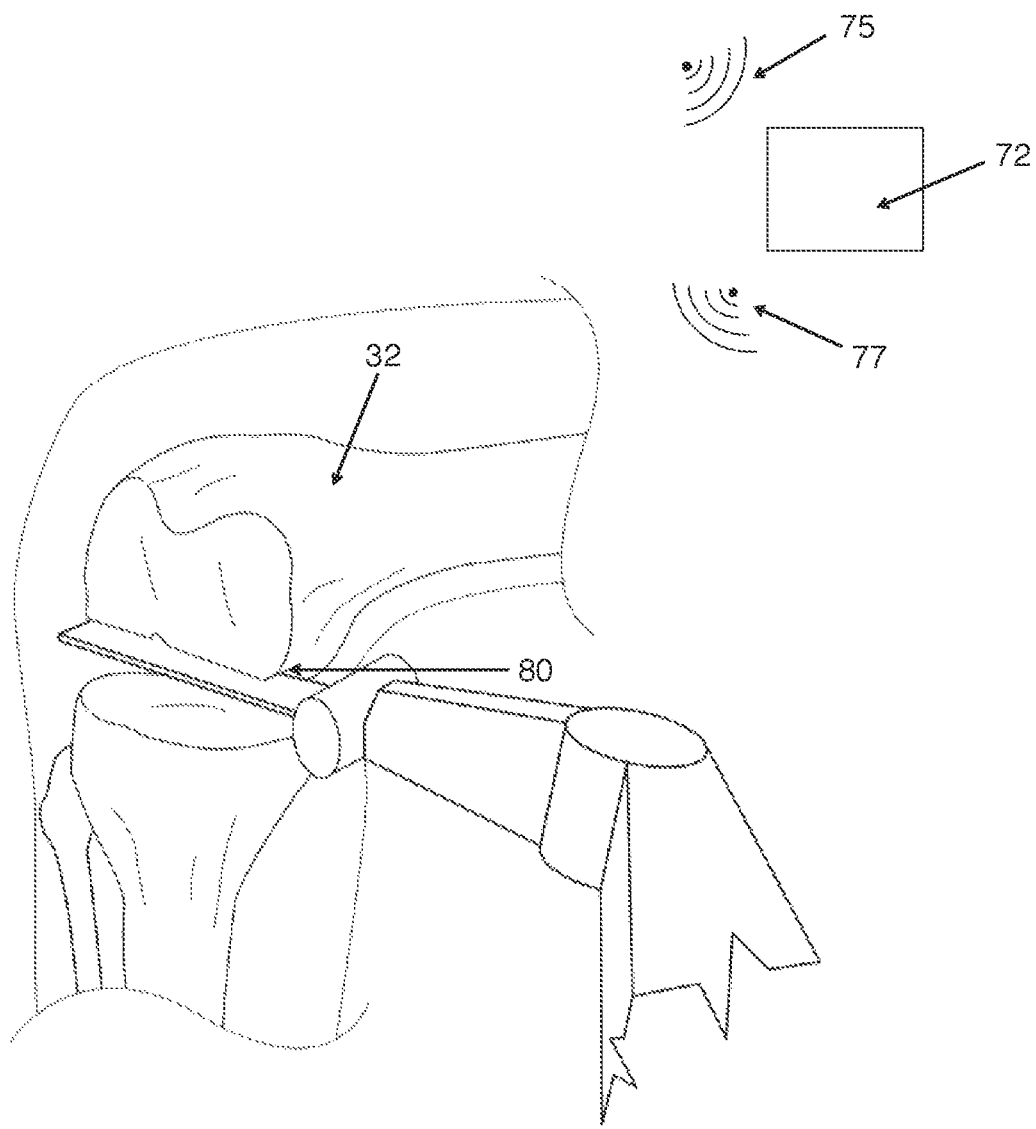

The height adjustability shown by way of arrows (21a) and (21b) for the height adjustable extension tabs (17a) and (17b) along with the lateral adjustability of the user-operable lateral extension tabs (15a) and (15b) shown by way of arrows (19a) and (19b) will establish the requisite distal end of the femur reference plane 70 shown in FIG. 3e, and the preparation of the posterior condylar reference plane 74 shown in FIG. 3f.

The preferred embodiment shows a series of slots (18) to which requisite tooling can engage in order to laterally and vertically adjust the lateral extension tabs (15a), (15b) and/or height adjustable extension tabs (17a) and (17b), again in the arrowed directions shown as (19a), (19b) or (21a) and (21b).

The positioning and operation of the slots (18) is not essential to the invention and can be achieved through a variety of design choices and tool operation to drive the lateral extension tabs (15a), (15b) and/or height adjustable extension tabs (17a) and (17b) including mechanically, hydraulically, electrically, electronically and/or through computer navigation, robotics or a pneumatic drive action arrangement.

The slots (18) simply signify that the relevant laterally adjustable extension tabs (15a) and (15b) and the height adjustable extension tabs (17a) and (17b) can be manipulated accordingly in order to orientate the front plate 12 and the sections (7a) and (7b) of the base plate relative to the generally L shaped femoral tibia stability gap alignment clamp (11) so that requisite distal end of the femur reference plane 70 shown in FIG. 3e and posterior condyle reference plane 74 shown in FIG. 3f can be established and to which, again as referenced above and to be explained shortly hereafter, that information is inputted into the Electronic System Arrangement 72 to control the robotic arm 78 and cutting blade 79 responsible for the final bone resections of the distal end of the femur and the posterior femoral condyle.

Firstly referring to the distal end of the femur reference plane (70) shown in FIG. 3(*e*).

As discussed above, surgeon adjustment of lateral extension tabs (15*a*) and (15*b*) have orientated the front plate (12) to present the distal end of the femur reference plane (70).

Importantly for this invention however it is how this established distal end of the femur reference plane (70) and the way in which it is replicated upon the surface of the distal end of the femur when the final bone resection has been completed.

In the preferred embodiment of the invention the electronic system arrangement (72) is adapted to respond to an inputted signal wherein that inputted signal into the electronic system arrangement (72) has identified, measured and/or allows the recording of the information of the distal end of the femur reference plane (70) so that the electronic system arrangement (72) is able to use that information in the control of the robotic arm (78) and the cutting blade (79) attached to the robotic arm (78).

In the illustrations the electronic system arrangement (72) is not intended to represent where it would be relative to the knee joint being operated.

The electronic system arrangement (72) is shown only for pictorial purposes to understand its use in the invention, in that in certain preferred embodiments the electronic system arrangement (72) could be incorporate into, at least in part, the components being used by the surgeon or the electronic system arrangement (72) could remain a separate entity utilised within a computer or other electronic operable devices.

The essence of this invention however is that once the end of the femur reference plane (70) and/or posterior condyle reference plane (74) has been established by the surgeon, the electronic system arrangement (72) is inherently adapted to be able to receive a signal which provides information of the established distal end of the femur reference plane (70) shown in FIG. 3 with the inputted signal shown as (71) and in the case of the posterior condyle reference plane (74) in FIG. 3(*f*) being inputted as the signal (75).

Again for pictorial reasons, in FIGS. 3(*e*) and 3(*g*) the electronic system arrangement (72) receives the inputted signal (71) which provides information of the distal end of the femur reference plane (70) wherein the electronic system arrangement (72), again shown pictorially as (73) sends out a control signal to the robotic arm (78) for the robotic arm (78) to be able to be positioned and to have the cutting blade (79) orientated such that resecting of the bone at or below the distal end of the femur once complete will replicate that same established distal end of the femur reference plane (70) shown in FIG. 3(*e*).

In the case of FIGS. 3(*f*) and 3(*h*) the established posterior condyle reference plane (74) is inputted as an appropriate signal (75) into the electronic system arrangement (72) wherein the electronic system arrangement (72) sends out a control signal (77) to the robotic arm (78) and the corresponding cutting blade (79) so that as seen in FIG. 3(*h*) the cutting blade (79) for the final resection cut provides for the same profiled surface as the poster condyle reference plane (74) referenced in FIG. 3(*f*).

Although not shown in the illustrations the electronic system arrangement (72) could include a sensor arrangement such as pressure sensors that would be incorporated into the generally 'L' femoral tibia stability gap alignment clamp (11), the front plate (12) and/or the base of the front plate (12). The information derived from the pressure sensors can then be sent as a signal to which the electronic system arrangement (72) for the electronic system arrangement (72) to action accordingly.

FIGS. 4*a*, 4*b* and 5*a* to 5*f* are schematic representations of a method by which the arrangement can be utilized in order to prepare and cut the final bone resection to the proximal surface of the tibia in a preferred embodiment of the invention.

Referring FIGS. 4 and 5*a* to 5*f*, the tibia and femoral stability gap preparation plate which forms part of the overall arrangement of the preparation of the proximal surface of the tibia for the tibia component of a prosthetic knee joint for this invention is referenced generally as 110.

The tibia and femoral stability gap preparation plate 110 in the preferred embodiment includes a base plate 112. The base plate 112 is configured to rest appropriately upon the initial cut 135 of the proximal surface of the tibia 127.

In the preferred embodiment there is also included the top plate or platform 122. However, the user operable height adjustable extension tabs 113, 114 and 115 and the associated tip 119, 120 and 121 can also directly engage the underside 143 of the joint liner 137, again as to be discussed in greater detail when referencing FIGS. 5*a* to 5*f*, in the preferred embodiments the top plate 122 will engage the underside 143 of the joint liner 137.

The user operable height adjustable extension tabs 113, 114 and 115 are in operable engagement with the rotatable knobs 116, 117 and 118. As referenced by arrows 145, 146 and 147 rotations of rotatable knobs 116, 117 and 118 translates to the vertical height adjustment of the tips 119, 120 and 121 of the corresponding user operable height adjustment extension tabs 113, 114 and 115.

Figure 4A:
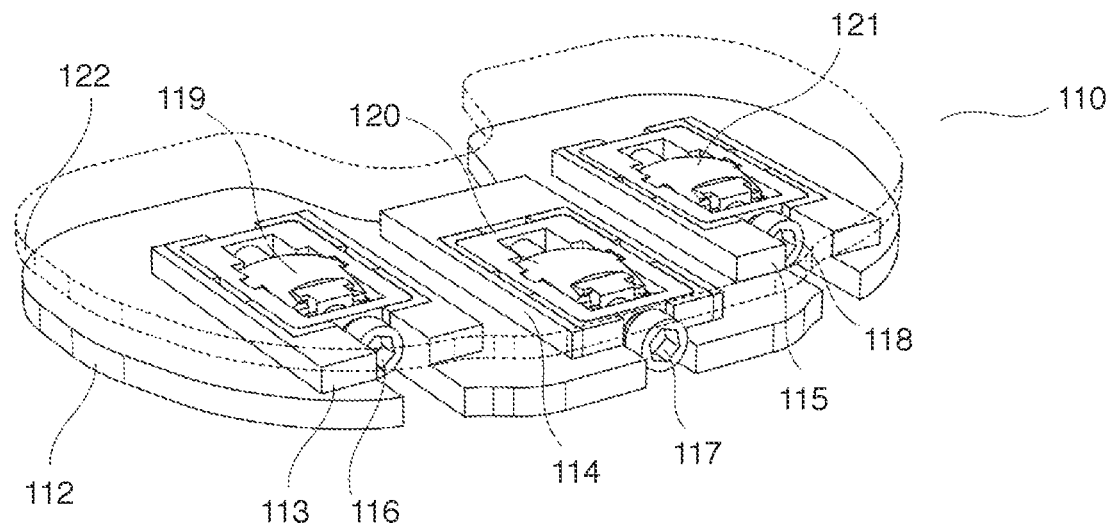
Figure 4B:
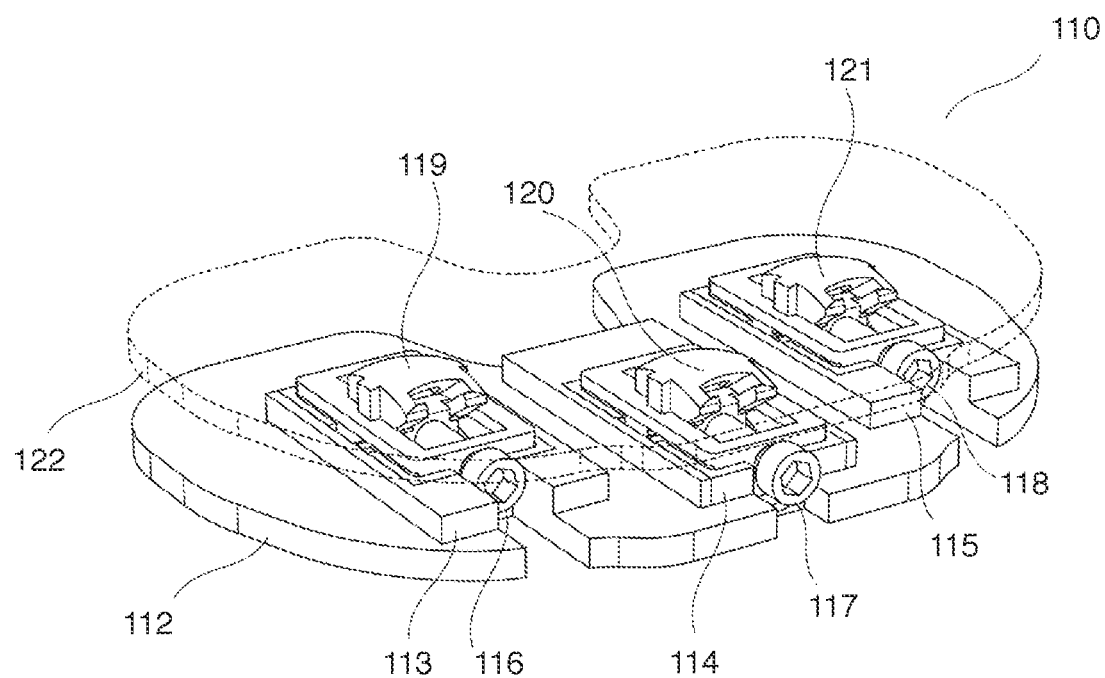
Figure 5A:
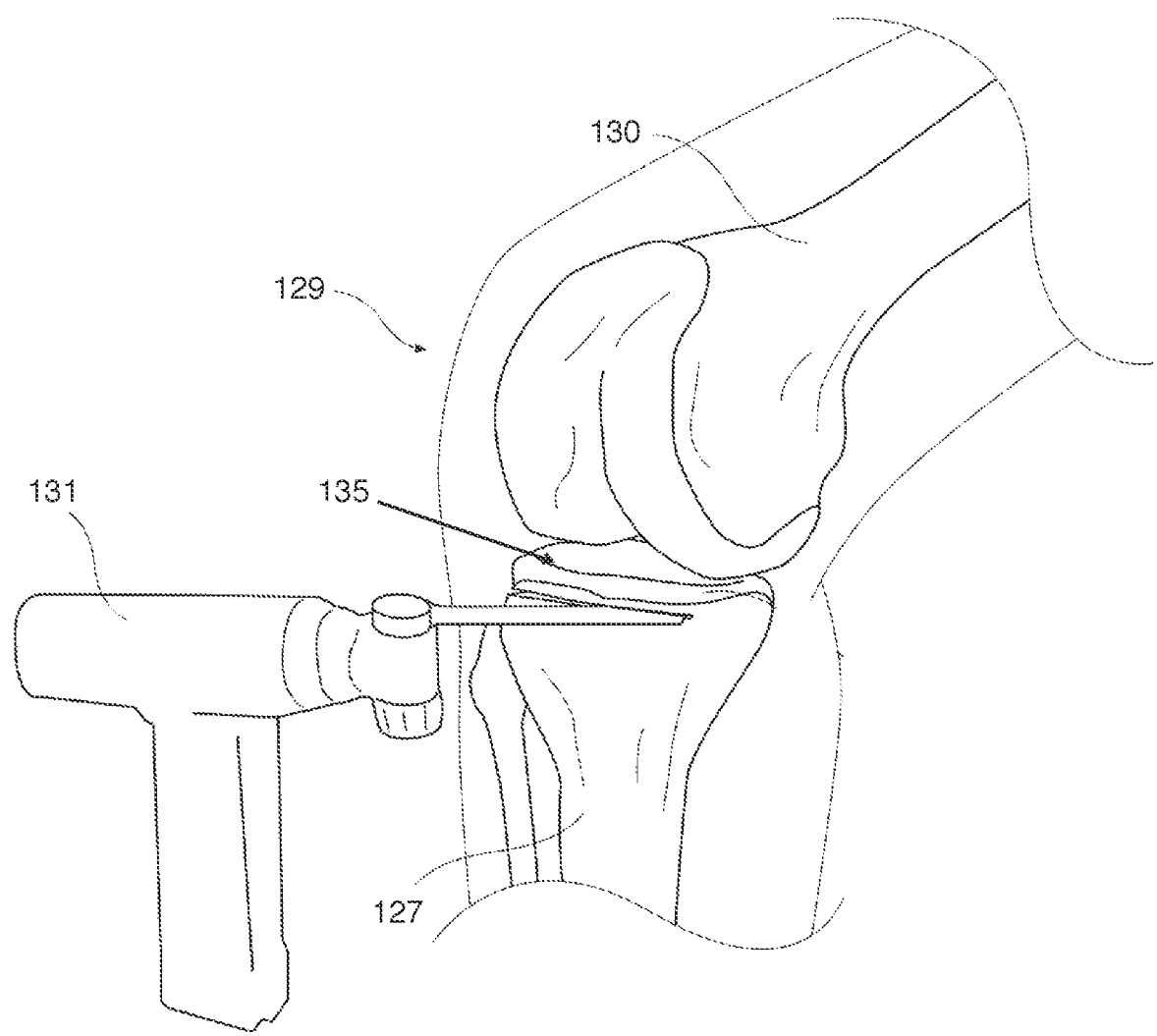
FIGS. 5a to 5f are schematic representations of a method by which the arrangement can be utilized in order to prepare and cut the final bone resection to the proximal surface of the tibia in a preferred embodiment of the invention.
Figure 5B:
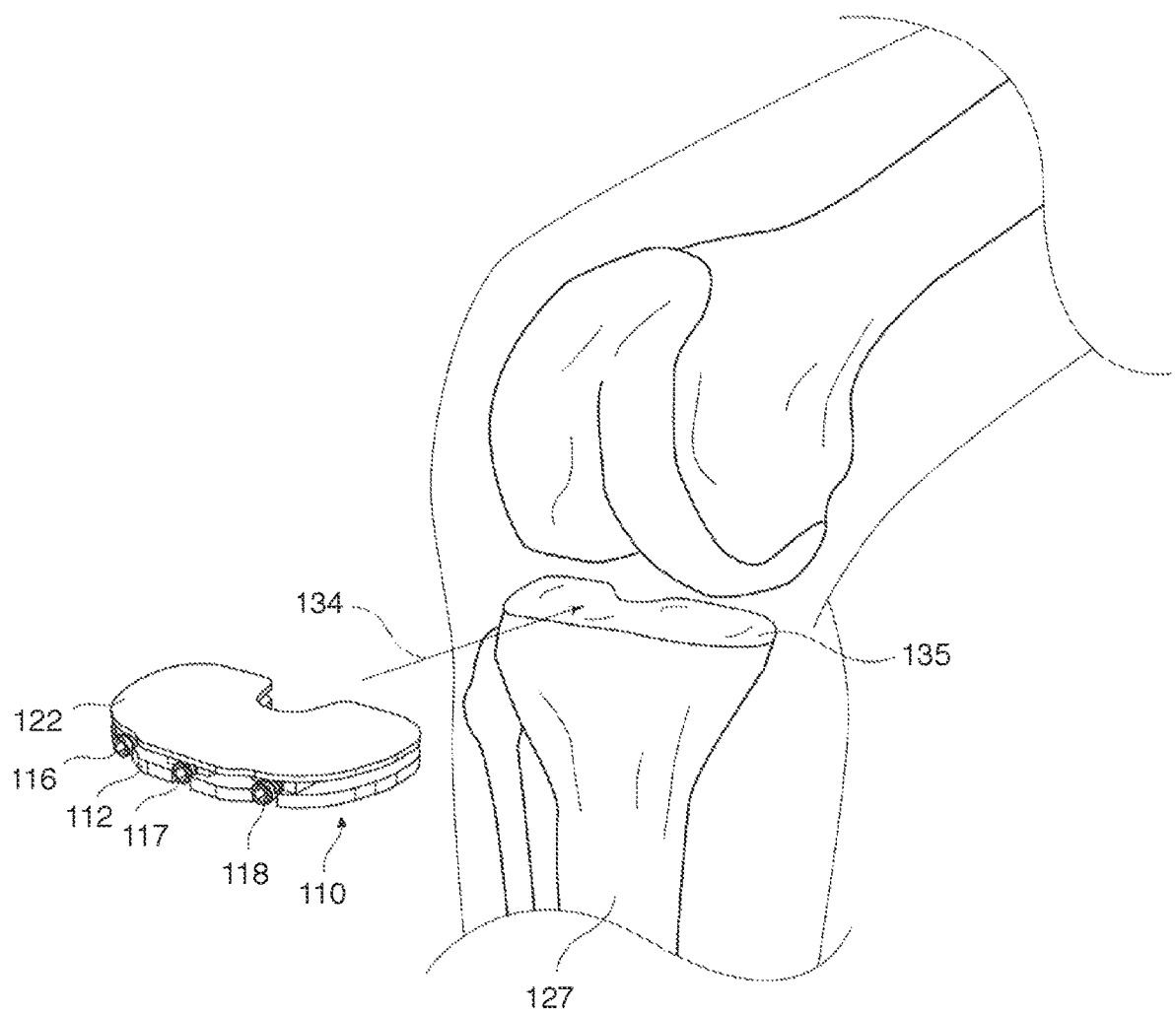
Figure 5C:
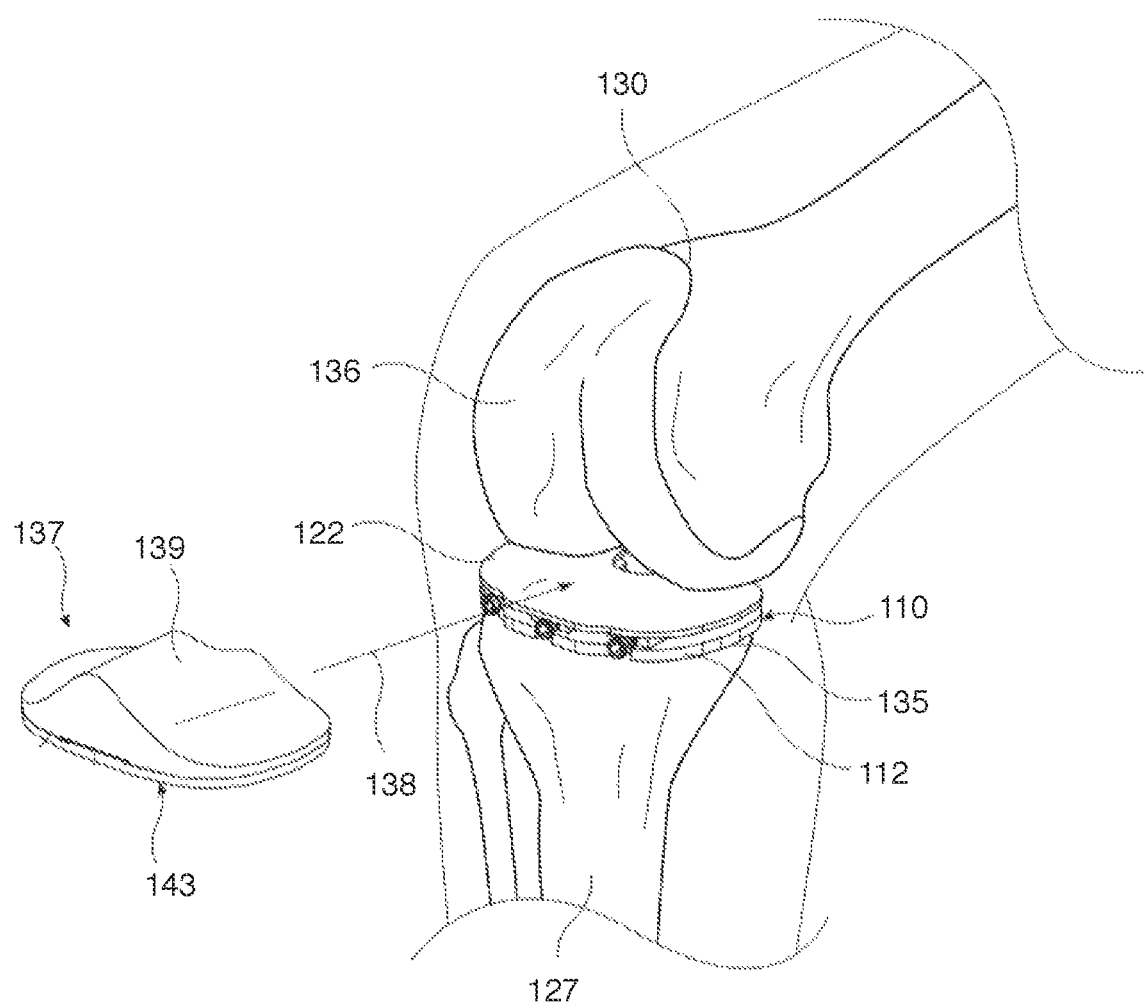
Figure 5D:
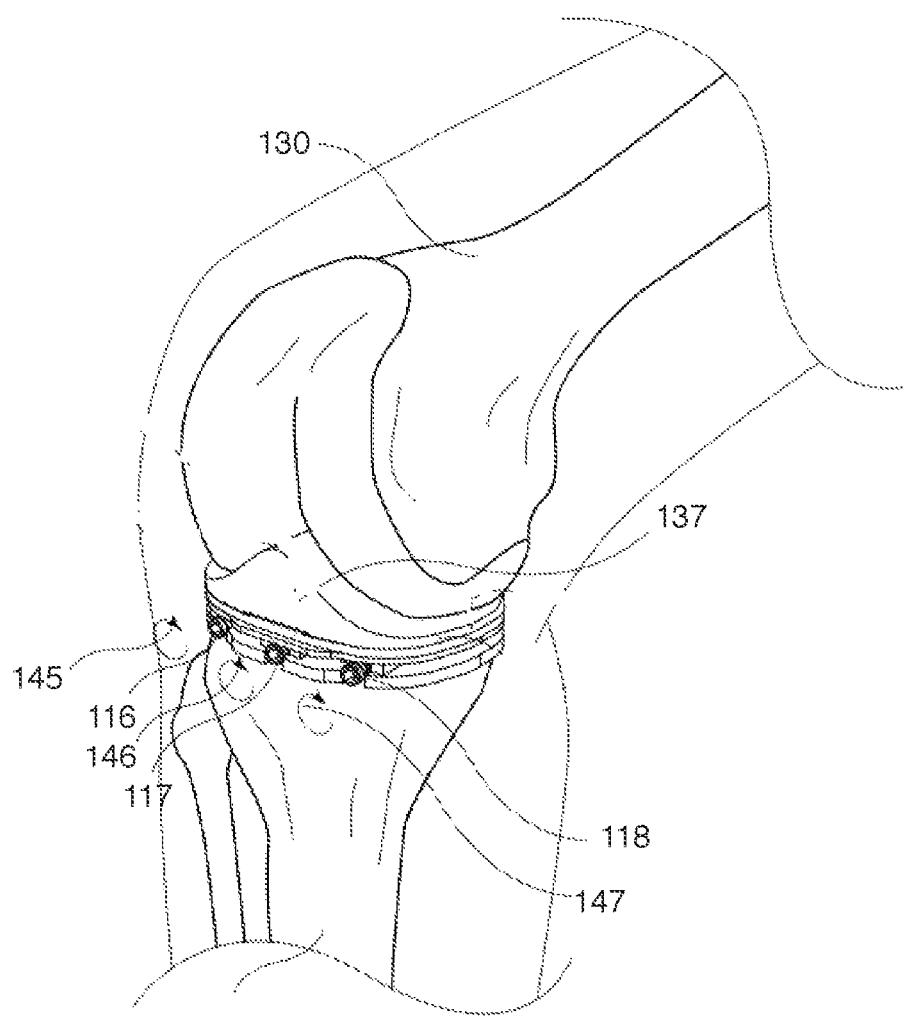
Figure 5E:
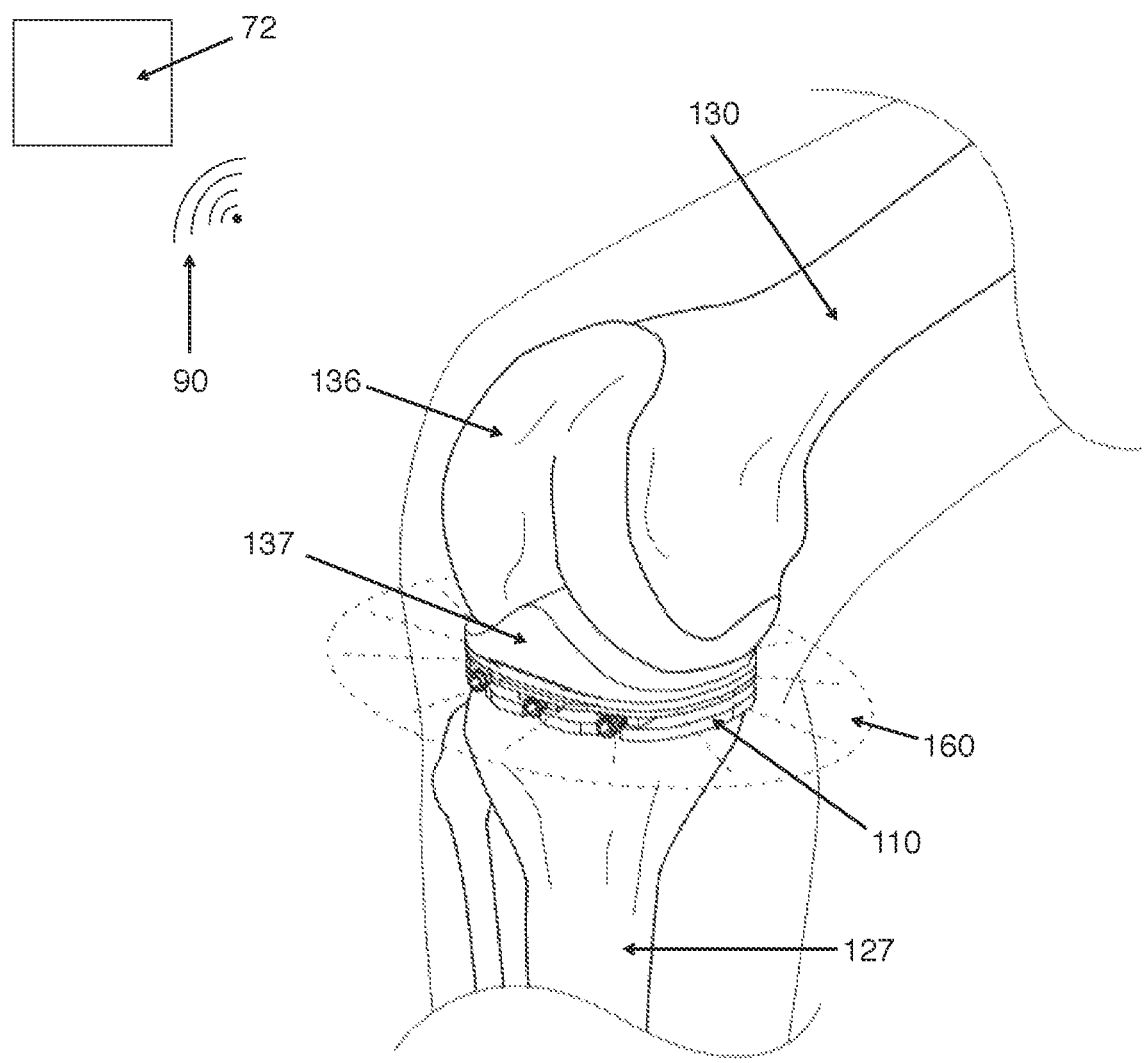
Figure 5F:
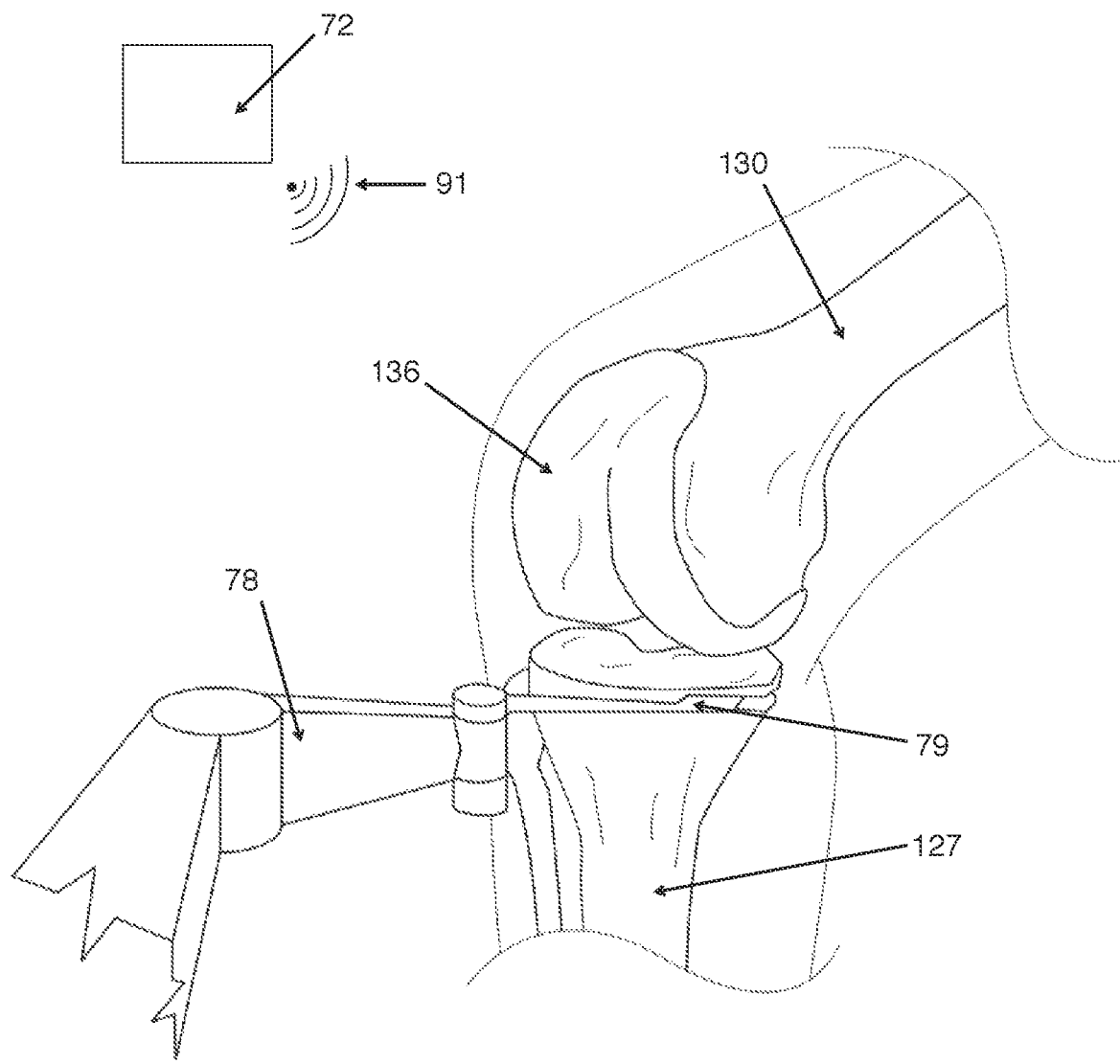

FIG. 4*a* shows tips 119, 120 and 121 of the user operable extension tabs 113, 114 and 115 in a lowered position and in FIG. 4*b* rotational movement of the user engagable knobs 116, 117 and 118 has seen the elevated height of the tips 119, 120 and 121 of the corresponding height adjustable extension tabs 113, 114 and 115 raised which is representative of their adjustability in order to establish the tibia reference plane 160 shown as broken lines in FIG. 5*e*.

By having three tips 119, 120 and 121 this provides for a triangulation which is establishing the appropriate tibia reference plane upon the plate 122 which will then be translated to the orientation of the underside 143 of the joint liner 137, to which plate 122 of the tibia and femoral stability gap preparation plate 110 engages.

The knee joint is shown generally as 129.

A cutter 131, prepares for the initial resection of the proximal surface 135 of the tibia 127. The general distal end of the femur 130 is also shown. The tibia and femoral stability gap preparation plate 110 shown by way of arrow 134 is being inserted onto the initially resected proximal surface 135 of the tibia 127.

In other preferred embodiments although not shown in the illustrations the cutter (131) can be included as part of a robotic arm arrangement to complete the initial resection, or in still other preferred embodiments the cutter (131) would include and/or work in combination with a hand saw, robotics, navigation, Patient specific cutting guides and the like.

It can realise that the general shape of the tibia and femoral stability gap preparation plate 110 is of a comparative dimension of the proximal surface 135 of the tibia 127.

FIG. 5c shows the actual positioning of tibia and femoral stability gap preparation plate 110 on the proximal surface 135 of the tibia 127 and to be sandwiched therein between the femoral component 136 and the tibia and femoral stability gap preparation plate 110 is the joint liner 137.

Arrow 138 is representative as to the location the joint liner 137 will be positioned in the knee joint 129.

The joint liner 137 has an articulated upper surface 139 to engage the femoral component 136 of the femur 130. 143 is representative of the under side of the joint liner 137.

FIG. 5d shows the knee joint at mid-flexion. Operable knobs 116, 117 and 118 when rotated by way of arrows 145, 146 and 147 though the height adjustable extension tabs, 113, 114 and 115 will adjust the orientation of the underside 143 of the joint liner 137.

This height adjustability although not shown in the illustrations would also have been completed at extension and then ultimately at flexion or 90 degrees.

Accordingly, the user operable height adjustable extension tabs 113, 114 and 115 create a triangular support of the top plate 122, which then aligns and/or orientates the underside 143 of the joint liner 137 accordingly. As shown in FIG. 5e the tibia references plane 160 that has now been established on the underside 143 of the joint liner 137 through the height adjustability of the height adjustable extension tabs 113, 114 and 115 from extension, mid-flexion and flexion.

With the tibia referenced plane 160 now established on the underside 143 of the joint liner 137, the final bone resection of the proximal surface of the tibia will require the same profiling as this tibia reference plane 160.

The invention claimed is:

1. An arrangement adapted to provide a final bone resection of a proximal surface of a tibia for a tibia component of a prosthetic knee joint, said arrangement including:
a tibia and femoral stability gap preparation plate, said tibia and femoral stability gap preparation plate adapted to be placed upon the proximal surface of the tibia, said tibia and femoral stability gap preparation plate further including an upper side, said upper side having a plurality of user operable height adjustable extension tabs, wherein each user operable height adjustable extension tab is adapted to engage an underside of a joint liner, wherein said joint liner includes an upper articulated surface adapted to engage a femoral component of a knee joint, such that a height adjustment of said plurality of user operable height adjustable extension tabs defines a measurement taken by a user in each of extension, mid-flexion and flexion, wherein the measurement is commensurate with a tibia reference plane defined on an underside of the joint liner,
an electronic system arrangement adapted to receive an input signal, wherein the input signal is derived from the measurement in each of extension, mid-flexion and flexion, and provides tibia reference plane measured data information, wherein the tibia reference plane measured data information includes orientation of the tibia reference plane defined by the underside of the joint liner;
said electronic system arrangement further configured to respond to the tibia reference plane measured data information provided by the input signal to communicate electrical energy in the form of an output action to align and move a blade and/or cutting implement in a cutting action that replicate the tibia reference plane on the proximal surface of the tibia when the final bone resection to the tibia is completed by the blade and/or cutting implement.

2. An arrangement adapted to provide a final bone resection proximal surface of a tibia for a tibia component of a prosthetic knee joint, said arrangement including:
a joint liner, wherein said joint liner includes an upper articulated surface to engage a femoral component of a knee joint, said joint liner on an underside side including a plurality of user operable height adjustable extension tabs, wherein each user operable height adjustable extension tab is adapted to engage the proximal surface of the tibia and/or a plate, platform or other generally flat object on the surface of the tibia, such that a height adjustment of said plurality of user operable height adjustable extension tabs defines a measurement taken by a user in each of extension, mid-flexion and flexion, wherein the measurement is commensurate with a tibia reference plane defined within and/or under the joint liner;
an electronic system arrangement adapted to receive an input signal, wherein the input signal is derived from the measurement in each of extension, mid-flexion and flexion, and provides a tibia reference plane measured data information, wherein the tibia reference plane measured data information includes orientation of the tibia reference plane defined by the within and/or under the joint liner;
said electronic system arrangement further configured to respond to the tibia reference plane measured data information provided by the input signal to communicate electrical energy in the form of an output action to align and move a blade and/or cutting implement in a cutting action that replicates the tibia reference plane on the proximal surface of the tibia when the final bone resection to the tibia is completed by the blade and/or cutting implement.

3. The arrangement of claim 1 or 2 wherein the electronic system arrangement includes a sensor arrangement to assist the user in defining the measurement taken by a user in each of extension, mid-flexion and flexion, wherein the sensor arrangement includes an accelerometer, gyroscope, a position sensor, an inductor sensor, a capacitive displacement sensor, laser sensor, optical sensor, pressure sensor, magnetic and magneto-inductor sensors, confocal sensors and/or draw-wire sensors and/or computer navigation.

4. The arrangement of claim 2 wherein the arrangement further includes a robotic arm, and the blade and/or cutting implement is attached to said robotic arm.

5. The arrangement of claim 4 wherein the robotic arm is under the control of the electronic system arrangement.

6. The arrangement of claim 1 or 2 wherein the electronic system arrangement includes and/or communicates with a display screen, to display measured information and/or action being carried out under control of said electronic system arrangement.

* * * * *